US009561009B2

(12) United States Patent
Woudstra et al.

(10) Patent No.: US 9,561,009 B2
(45) Date of Patent: Feb. 7, 2017

(54) MOBILE X-RAY UNIT

(71) Applicant: NUCLETRON OPERATIONS B.V., Veenendaal (NL)

(72) Inventors: Bas Woudstra, Vaassen (NL); Wim De Jager, Rhenen (NL)

(73) Assignee: Nucletron Operations B.V., Veenendaal (NL)

( * ) Notice: Subject to any disclaimer, the term of this patent is extended or adjusted under 35 U.S.C. 154(b) by 0 days.

(21) Appl. No.: 14/971,981

(22) Filed: Dec. 16, 2015

(65) Prior Publication Data
US 2016/0100813 A1   Apr. 14, 2016

Related U.S. Application Data

(63) Continuation of application No. 13/335,286, filed on Dec. 22, 2011, now abandoned.
(Continued)

(30) Foreign Application Priority Data

Dec. 22, 2010   (NL) ..................... 2005906

(51) Int. Cl.
*A61N 5/10* (2006.01)
*A61B 6/00* (2006.01)
(Continued)

(52) U.S. Cl.
CPC .............. *A61B 6/4405* (2013.01); *A61B 6/06* (2013.01); *A61N 5/10* (2013.01); *H05G 1/26* (2013.01);
(Continued)

(58) Field of Classification Search
CPC ..................................................... A61N 5/10
See application file for complete search history.

(56) References Cited

U.S. PATENT DOCUMENTS 8,520,801 B2   8/2013 Henning
2003/0048875 A1*   3/2003 Mihara ................... A61N 5/10
378/196
(Continued)

FOREIGN PATENT DOCUMENTS

WO   WO2008/118198   10/2008

OTHER PUBLICATIONS

Search Report and Written Opinion in related Netherlands Application No. 2005906 dated May 28, 2011 (8 pages).
(Continued)

*Primary Examiner* — David J Makiya
*Assistant Examiner* — Dani Fox
(74) *Attorney, Agent, or Firm* — Finnegan, Henderson, Farabow, Garrett & Dunner, LLP

(57) ABSTRACT

One embodiment of the present disclosure is directed to a mobile X-ray unit. The mobile X-ray unit may include a base accommodating a control unit for controlling an X-ray applicator and a power supply for supplying power to the X-ray applicator. The mobile X-ray unit may further include an arm associated with the base. The arm may be configured to support an X-ray applicator having an X-ray tube. The arm may be articuable. The X-ray tube may include a target element configured to generate an X-ray beam and a collimator configured to shape the X-ray beam. The target element may be disposed at a set distance from the collimator.

20 Claims, 13 Drawing Sheets

Related U.S. Application Data

(60) Provisional application No. 61/426,896, filed on Dec. 23, 2010.

(51) Int. Cl.
  *A61B 6/06* (2006.01)
  *H05G 1/26* (2006.01)
  *A61N 5/00* (2006.01)

(52) U.S. Cl.
  CPC ........ *A61N 5/1083* (2013.01); *A61N 2005/005* (2013.01); *A61N 2005/1056* (2013.01); *A61N 2005/1091* (2013.01)

(56) References Cited

U.S. PATENT DOCUMENTS

| | | |
|---|---|---|
| 2007/0076851 A1 | 4/2007 | Pellegrino |
| 2008/0107239 A1* | 5/2008 | Sayeh ................. A61N 5/10 378/148 |
| 2008/0187099 A1 | 8/2008 | Gertner |

OTHER PUBLICATIONS

Topex, Inc., "SRT 100 Superficial Radiotherapy System for the Treatment of Skin Cancer," http://www.harpell.ca/wp-content/uploads/2009/11/topexbrochure_v10.pdf, (6 pages).

Topex, Inc., "Regulatory Information," http://www.topexmedical.com/product2.html, 2007 (1 page).

\* cited by examiner

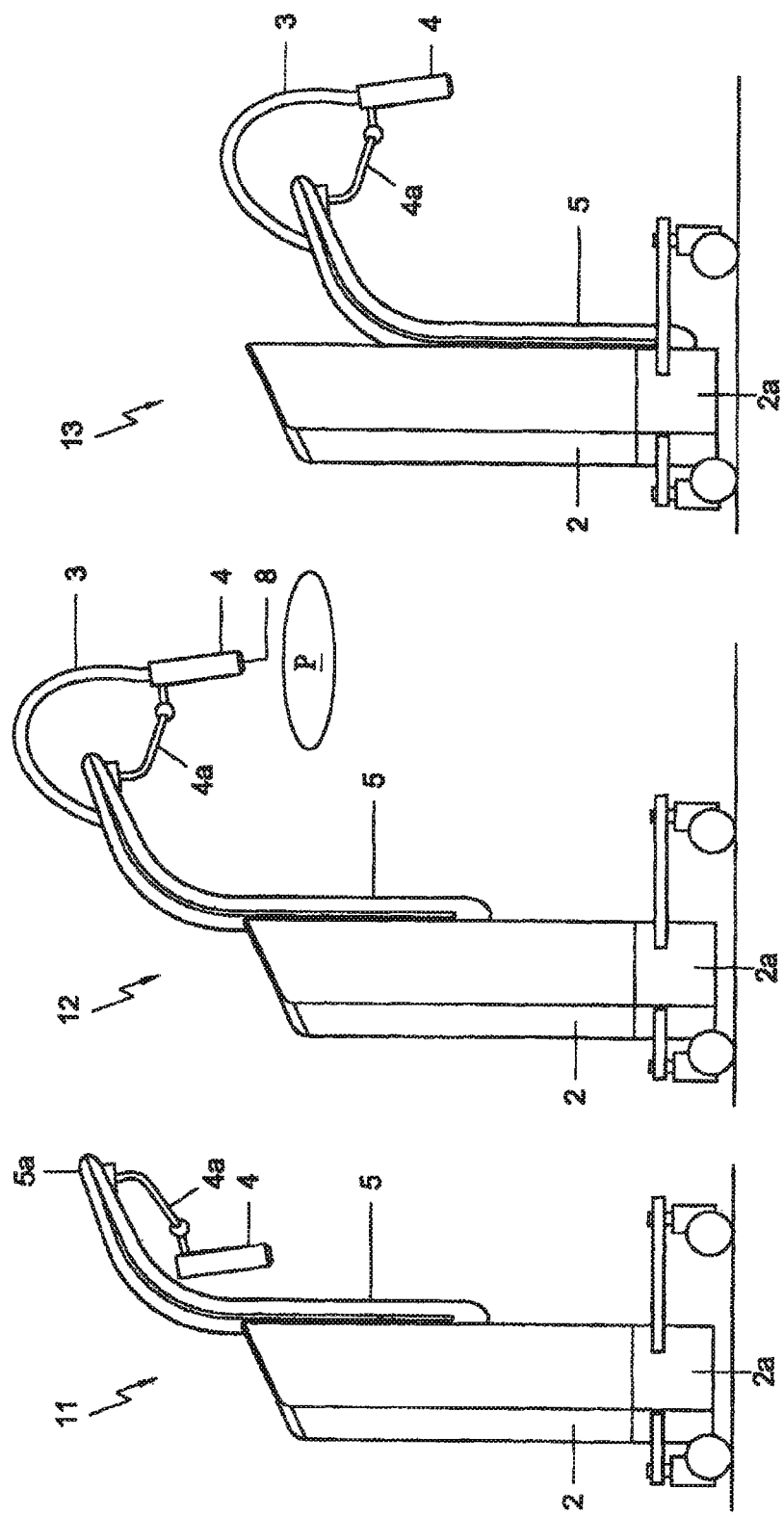

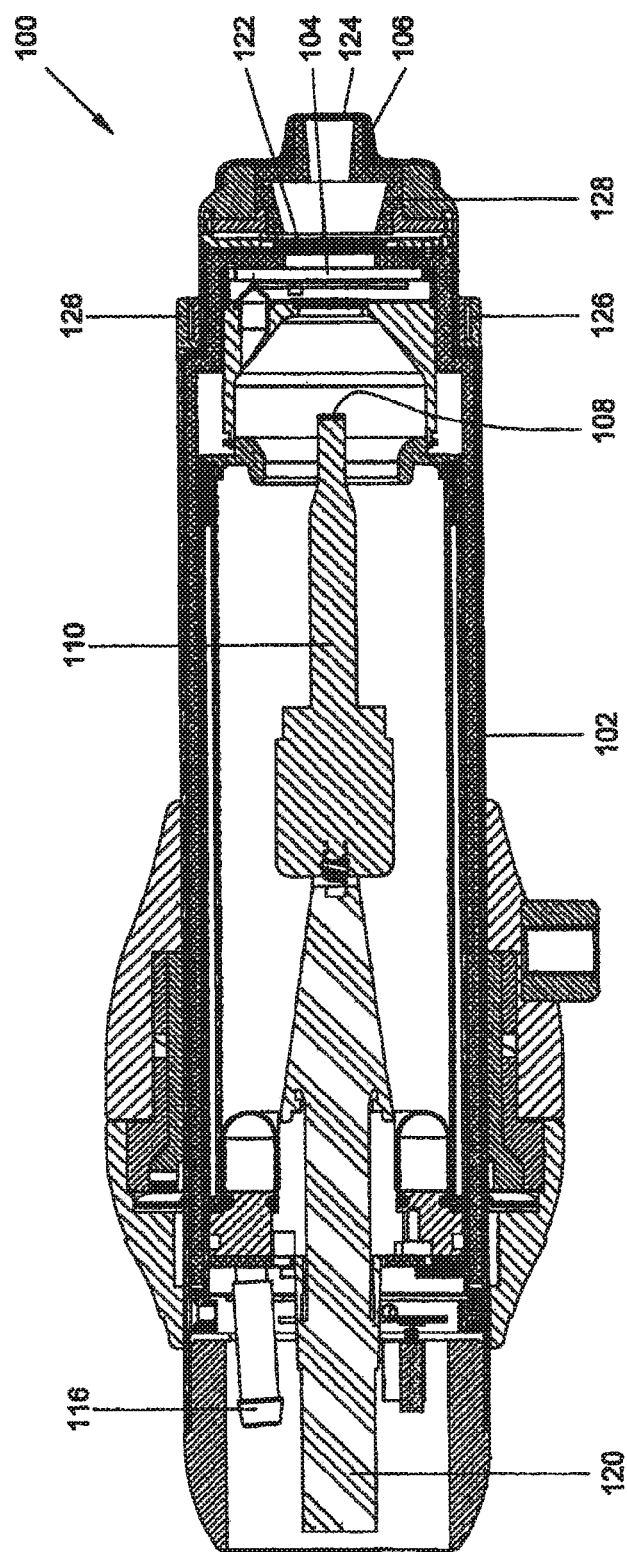
Fig. 7, E-E

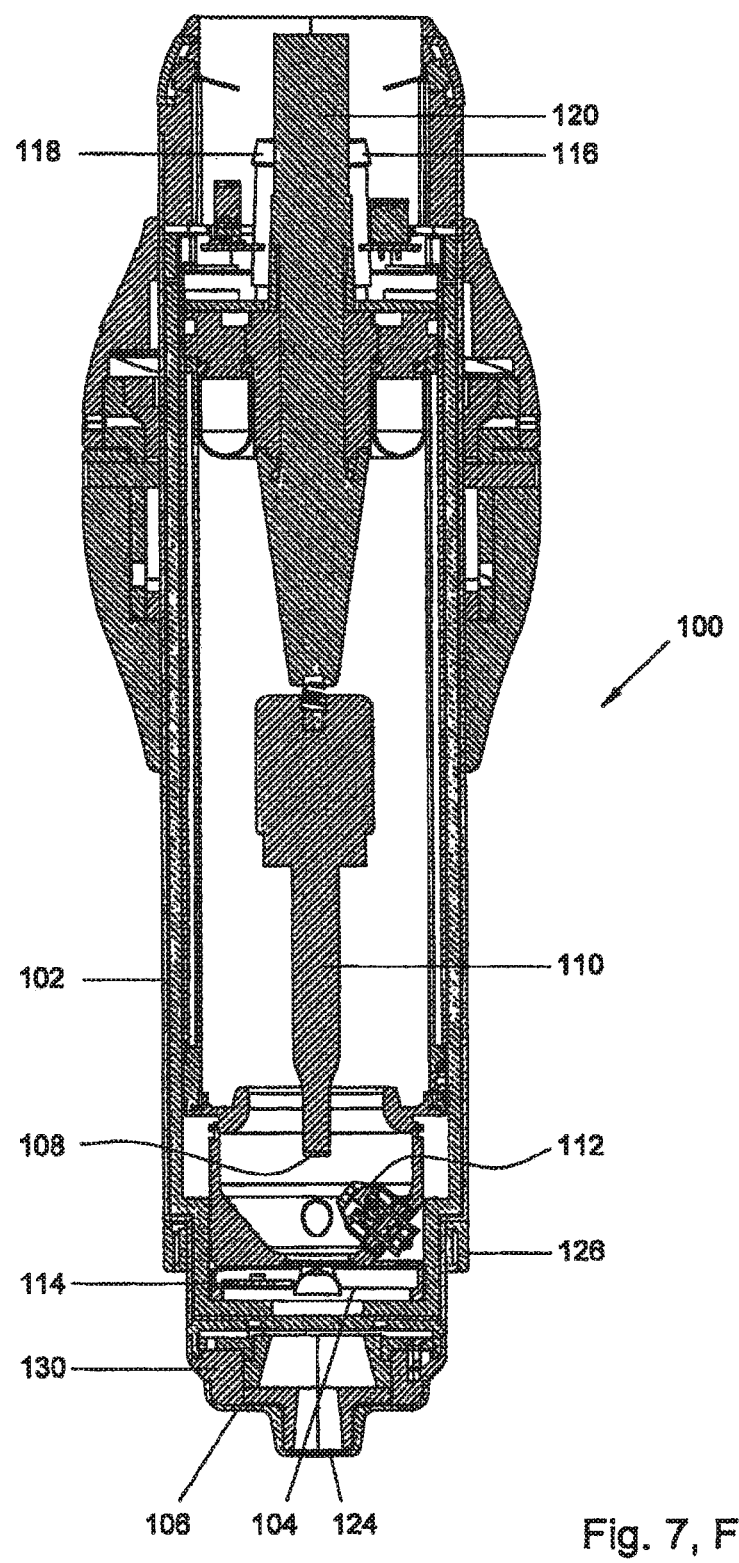
Fig. 7, F-F

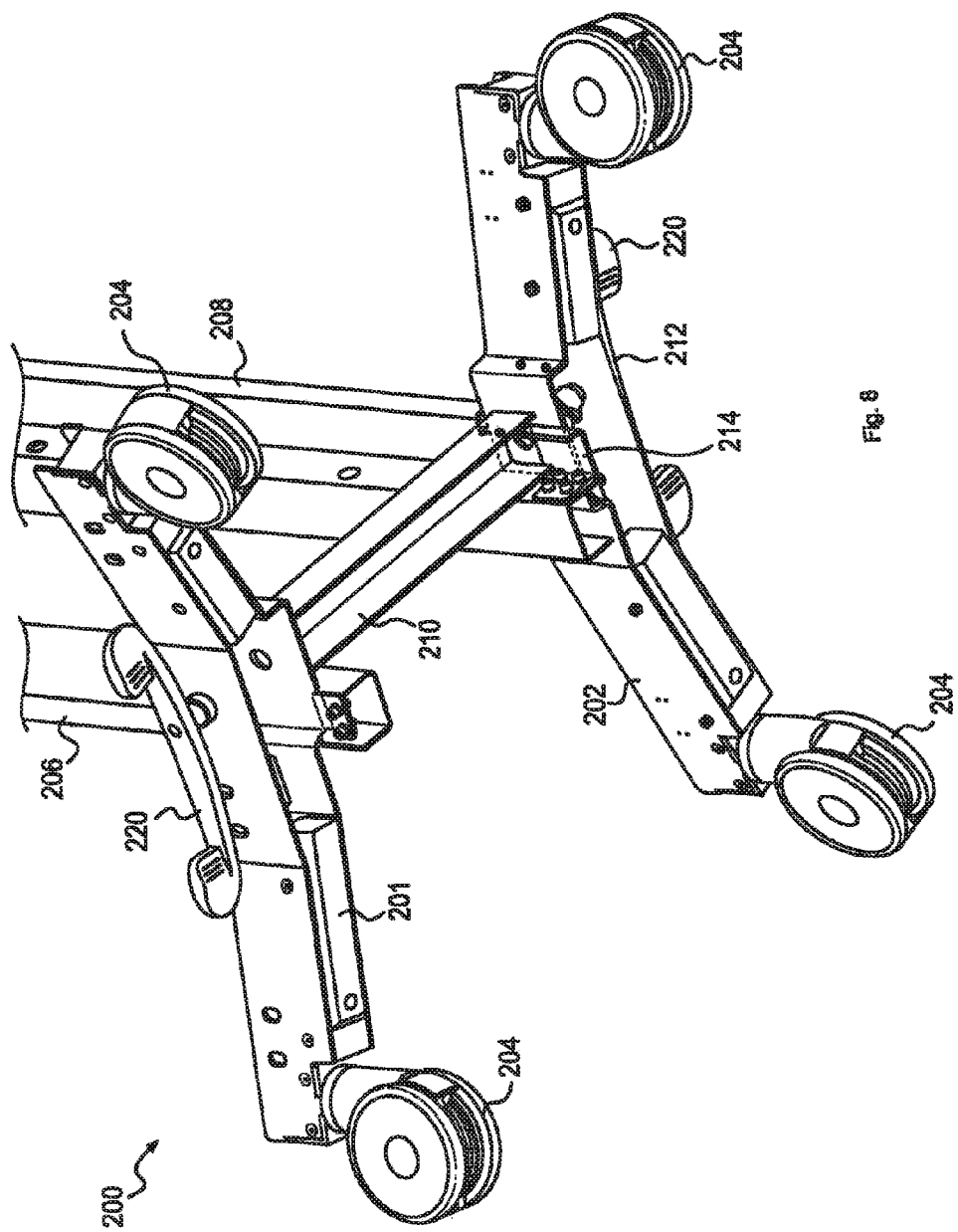

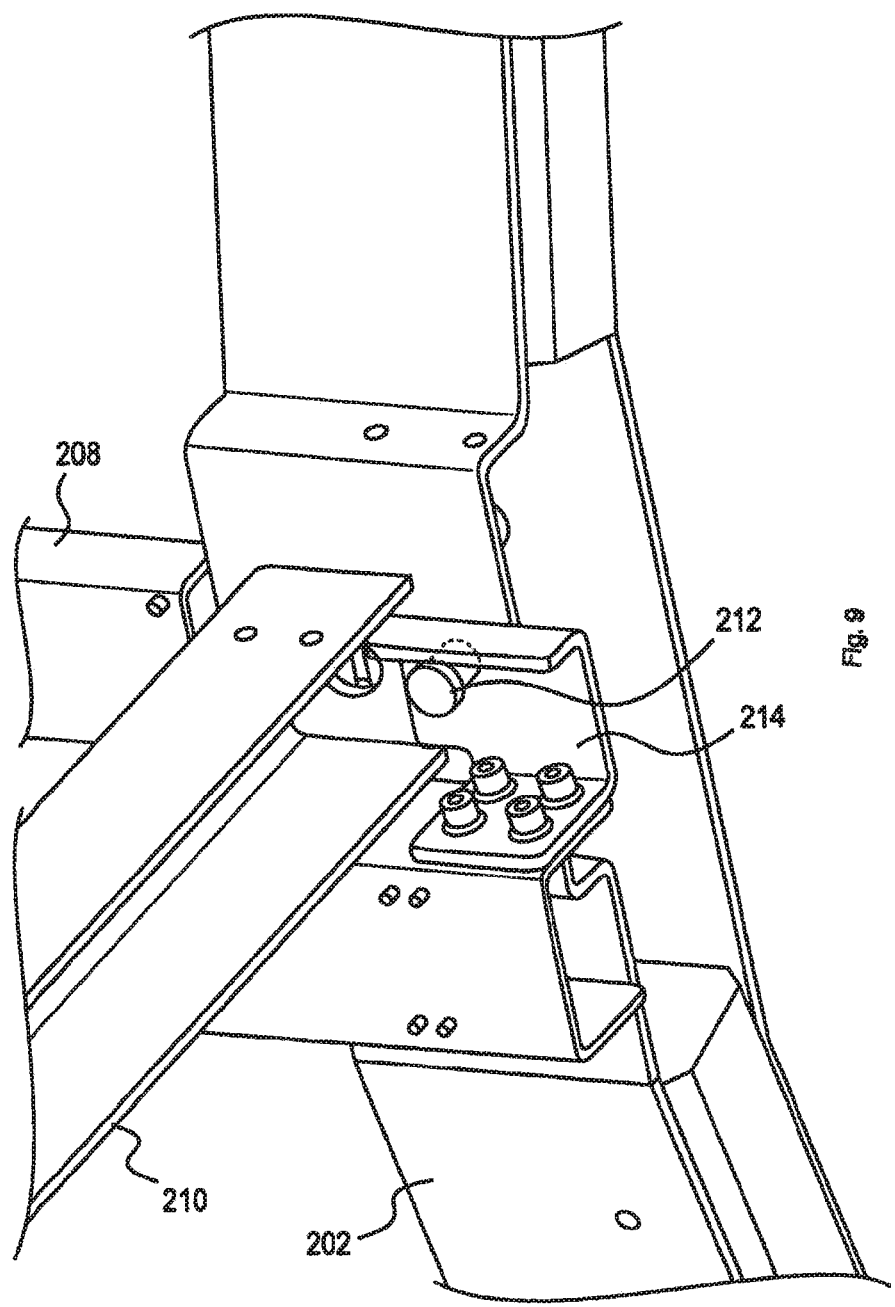

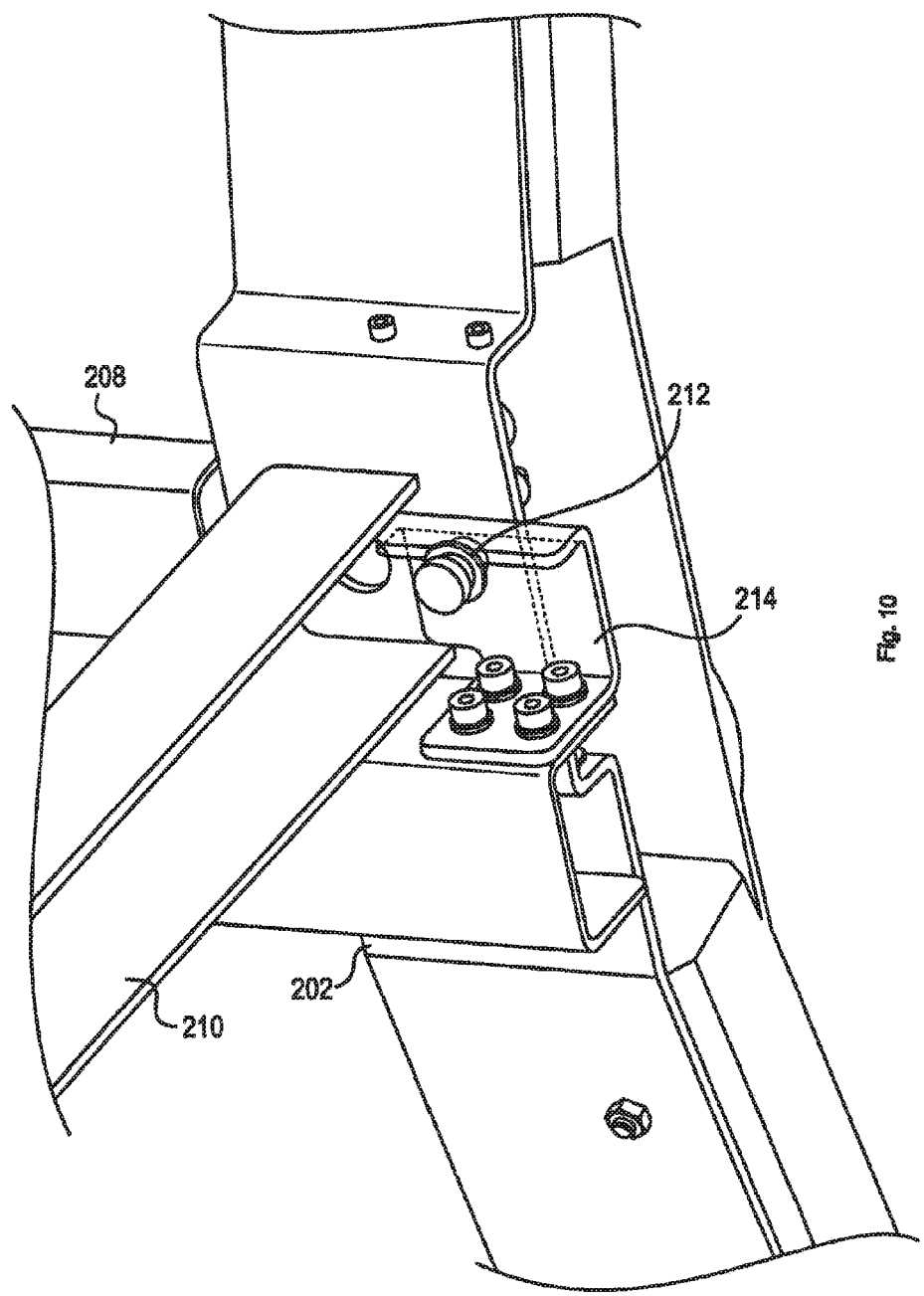

MOBILE X-RAY UNIT

CROSS-REFERENCE TO RELATED APPLICATIONS

This is a continuation of U.S. application Ser. No. 13/335,286, filed Dec. 22, 2011, which claims the benefit of priority based on U.S. Provisional Patent Application No. 61/426,896, filed Dec. 23, 2010, and Netherlands Patent Application No. 2005906, filed Dec. 22, 2010, which are all incorporated herein by reference in their entirety.

FIELD OF THE INVENTION

The present disclosure relates generally to a medical care unit, and, more particularly, a mobile X-ray unit. The present disclosure further relates to a method of manufacturing the mobile X-ray unit, and a method of delivering an X-ray beam from a mobile X-ray unit.

BACKGROUND OF THE INVENTION

The incidence rate of skin cancer has substantially increased in the last decade of the 20$^{th}$ century. It is appreciated that over 1.3 million new skin cancers are diagnosed annually, which is increasing at a rate of about 5% per year. Increased exposure to the sun without skin protection and a decreased ozone layer are regarded as the main causes of this increase—a problem estimated to be costing over 1 billion Euros in annual medical treatment expenses. Over 80% of skin cancers occur in the head and neck regions with 50% occurring in patients over 60 years of age. It is expected that a portion of the senior population will double in year 2025 compared to the present demographics. Because of the growing incidence of skin cancer and increasing share of the senior population in the overall demographics, much focus has been placed on cancer treatments and cancer treatment logistics.

Non-proliferative cancers, which are defined by substantially superficial lesions, may be treated in different ways. In one example, non-proliferative cancers may be treated surgically. Surgery, however, may have certain drawbacks, such as, for example, long waiting lists, complications related to post-treatment care, and risk of infection. Alternatively, patients may undergo irradiation using electrons of soft X-rays. Irradiation may have an advantage of being non-invasive and of a short duration (a treatment session may be as short as 2 to 4 minutes). It will be appreciated that usually the integral treatments using radiotherapeutic techniques may require a number of sessions.

Recently, the use of a mobile and portable X-ray unit has been suggested, which may be used inside a hospital radiotherapy department. An embodiment of such a unit is described in US 2007/0076851. Existing X-ray units include an X-ray source and a filtering device having a plurality of filters rotatably arranged with respect to a focal point of the X-ray tube for changing filtering characteristics on demand. The plurality of filters are arranged in a filtering device, which is transversely arranged with respect to a longitudinal axis of the X-ray tube. These units, while effective, may have certain drawbacks. For example, X-ray beam characteristics may be affected by the internal geometry of the X-ray tube, leading to, for example, a broadened penumbra of the X-ray beam.

SUMMARY OF THE INVENTION

It is an object of the disclosure to provide a mobile X-ray unit having improved operational characteristics. In particular, it is an object of the disclosure to provide a mobile X-ray unit having an improved penumbra of the X-ray beam and/or a reduced skin dose, when dose delivery is specified at 5 mm depth. It will be appreciated that the terms 'mobile' and 'portable' in the context of the present application may be interchanged as these terms equally relate to an easily moved or transported device, for example, a device which may be moved or transported by a single individual.

In accordance with one embodiment of the present disclosure, the mobile X-ray unit may include a target and a collimator, where a distance between the target and the collimator may be in a range between 4 and 10 cm. It is found that by setting a distance between the X-ray target and the collimator at a distance in the range between 4 and 10 cm, and more preferably at a distance in the range between 5 and 6 cm, may improve the X-ray beam characteristics. In particular, a distance of 4 to 10 cm between the X-ray target and the collimator, and preferably a distance of 5 to 6 cm, may reduce the focal size, thereby providing an improved beam flatness as well as providing a sharpened penumbra. For example, for the target-collimator distance of about 5 cm, a penumbra of 1.5 to 1.8 mm may be achieved (specified for 20/80% lines).

It is appreciated that a sharpened penumbra is important particularly for treating of small lesions, like skin cancers, so as to minimize treatment of healthy tissue.

In various embodiments of the present disclosure, the target and the collimator may be received in a substantially cylindrically shaped X-ray tube having a longitudinal axis. A direction of propagation of the X-ray beam may be substantially parallel to the longitudinal axis of the X-ray tube.

The arrangement of the anode-collimator geometry may be advantageous. In particular, the axis of the X-ray tube may substantially coincide with a direction of propagation of the generated X-ray beam. The arrangement may permit the x-ray tube and an x-ray applicator to have the same longitudinal axis. Furthermore, the configuration may be advantageous from a mechanical perspective. In particular, the applicator may be balanced on the articulated arm in a simplified manner. It will be appreciated that the X-ray tube, disposed in the X-ray applicator, represents a relatively slim (outer diameter of less than 10 cm) elongated cylinder (length of about 30 cm), which is preferably displaced in a vertical direction for delivering the X-ray beam to the patient. Once the internal geometry of the X-ray tube is co-axial, the weight of the X-ray tube may be suitably balanced enabling easy and reproducible displacement of the articulated arm supporting the X-ray applicator.

In various embodiments of the present disclosure, the collimator may be provided with an automatic identification device configured to generate a signal in the control unit representative of collimator characteristics.

It may be advantageous to have an automatic method of identifying when the collimator has been inserted in the X-ray tube so as to minimize or eliminate human errors in defining the field geometry. For example, the collimator may be positioned in a receptacle having a resistive path whose resistivity may be changed. The collimator may be arranged with projections adapted to cooperate with the resistive path of the receptacle for changing the resistivity of the receptacle, and thus, generating a signal indicating that the collimator has been inserted into the receptacle. In some embodiments, the signal may be transmitted to the control unit of the mobile X-ray unit for independent verification. It is contemplated that the mobile X-ray unit comprises a set of collimators each having identification devices.

In various embodiments of the present disclosure, the mobile X-ray unit may include a signaling device configured to indicate that an X-ray beam has been generated.

It may be advantageous to provide a signaling device that indicates the operational state of the X-ray beam. In some embodiments, the signaling device may be implemented as a suitable light on the X-ray applicator. One or more light emitting diodes may be used for this purpose. It may be possible to provide a plurality of signaling devices that indicate the energy of the generated X-ray beam.

For example, for the X-ray beam of a lower portion of the spectrum (about 50 kV), a first indicator may be used, such as, for example, a first light color. For an intermediate portion of the spectrum (about 60-65 kV), a second indicator may be used, such as, for example, a second light color. Finally, for the higher portion of the spectrum (66-75 kV, preferably 66-70 kV), a third indicator may be used, such as, for example, a third light color. It will be appreciated that a plurality of possibilities exist for indicating different spectra, including but not limited to a progressive illumination of a plurality of indicators upon hardening of the delivered X-ray beam. It will be further appreciated that such indication of the kV range may be disposed in the device, in a user interface, or in a supplementary unit. It will be further appreciated that the named kV ranges may be scaled with, for example the factors 1:1; 1:2; 1:3; 1:4; and 1:5. In some embodiments, the signaling device is a light indicator arranged on an outer housing. Such an arrangement of the signaling device may be advantageous as the patient is made aware about the starting point and the termination of irradiation so that the patient may retain a static position during the course of treatment.

In various embodiments of the present disclosure, the mobile X-ray unit may include a cooler arranged with piping to provide a cooling medium in a vicinity of the X-ray tube. The piping may run in a space between the X-ray tube and a shielding wall associated with the X-ray tube.

It may be advantageous to provide a space between the outer surface of the X-ray tube and the inner surface of the X-ray tube, that is at least partially filled with a coolant. In some embodiments, it may be advantageous to provide circulated water as a cooling agent due to high specific heat capacity, offering improved heat transfer of water with respect to a gas. However, pressurized gas may also be used as a suitable coolant. In some embodiments, a temperature sensor is arranged on the outer housing of the X-ray applicator for measuring actual temperature of the outer housing. The temperature sensor may be connected to the control unit for controlling the cooler and/or for controlling the high voltage supply. Should the temperature rise above a predetermined shut-off value, the control unit may be arranged to disable the high voltage supply and/or to intensify the cooling mode, for example, by increasing a pumping capacity of the coolant.

In various embodiments of the present disclosure, a radiation detector may be provided inside the outer housing for detecting the X-ray beam.

It may be advantageous to provide an independent radiation detector for detecting the presence of the generated X-ray beam. In some embodiments, the mobile X-ray unit includes a primary timer which sets a time for the high voltage supply for delivering a predetermined radiation dose. The radiation sensor accommodated inside the outer housing of the X-ray applicator may be part of a secondary timer circuit adapted to shut down the high voltage supply after the predetermined radiation dose is delivered. In this way radiation safety control may be improved.

In various embodiments of the present disclosure, the X-ray applicator may include an exit surface directed towards a patient. The surface being covered by an applicator cap.

It may be advantageous to provide an applicator cap, which may have many functions in use. In one example, the applicator cap may be used for protecting the exit surface of the X-ray applicator from intra-patient contamination. In another example, the thickness of the cap in a direction of the beam propagation may be sufficient for substantially eliminating electron contamination from the X-ray beam. Those skilled in the art will readily appreciate the relationship between the energy of the secondary electrons emitted from the X-ray tube and a required thickness of a given material, such as, for example plastic, glass, and ceramics, sufficient to fully intercept these electrons. In some embodiments, the applicator cap may be disposable.

In yet another example, the applicator cap may function as a heat absorber to dissipate the elevated temperature of the X-ray applicator. As a result the patient will feel the applicator contacting the skin as a slightly warm object.

In various embodiments of the present disclosure, the X-ray applicator may be connected to the base using a displaceable panel. Flexible cabling connecting the base to the X-ray applicator may run substantially in the displaceable panel.

It may be advantageous to provide an intermediate mechanical unit connecting the base of the mobile X-ray unit and the X-ray applicator for housing the flexible cables thereby preventive their entanglement. The displaceable panel may be arranged with a pre-defined travel distance with respect to a lowest achievable stand position and a highest achievable stand position. Such predefined travel distance may be advantageous for increasing durability of the cables tubes and wiring of the X-ray unit, especially of the tubes accommodating the coolant.

In various embodiments of the present disclosure, the displaceable panel may include a user interface for controlling the mobile X-ray unit. In some embodiments, the user interface may be a display. For example, the display may be implemented as a touch screen arranged for enabling data input. Alternatively, the display may be arranged for echoing data. In this embodiment, dedicated buttons or other suitable means may be provided for entering input data into the mobile X-ray unit.

Another embodiment of the present disclosure is directed to a method for manufacturing a mobile X-ray unit. The mobile X-ray unit may include a base for accommodating a control unit, a power supply, and a cooler. The mobile X-ray unit may further include an articulated arm supporting an X-ray applicator having an X-ray tube. The method may include connecting the arm to the base using a flexible cable. The method may further include arranging within the X-ray tube a target for generating an X-ray beam, and a collimator for shaping the generated X-ray beam. The method may further include setting a distance between the target and the collimator in a range between 4 and 10 cm.

In various embodiments of the present disclosure, the target and the collimator may be accommodated in a substantially cylindrically shaped X-ray applicator having a longitudinal axis. A direction of propagation of the X-ray beam being substantially parallel to the longitudinal axis. Further advantageous embodiments of the method according to the disclosure will be discussed with reference to FIG. 3.

Another embodiment of the present disclosure is directed to a method of delivering an X-ray beam for irradiating a superficial lesion. The method may include providing an X-ray unit including a base for accommodating a control unit, a power supply, and a cooler. The X-ray unit may further include an articulated arm accommodating an X-ray tube. The arm may be connected to the base using a flexible cable. The X-ray tube may include a target for generating an X-ray beam and a collimator for shaping the generated X-ray beam. A distance between the target and the collimator may be in the range 4 and 10 cm.

Another embodiment of the present disclosure is directed to applicator cap for an X-ray unit including an X-ray tube accommodated in an X-ray applicator. The X-ray applicator may include an exit surface oriented towards a patient, the applicator cap being arranged for covering at least the exit surface. In some embodiments, the applicator cap may be disposable. In some embodiments, a thickness of the cap in a direction of the beam propagation may be sufficient for substantially eliminating electron contamination from the X-ray beam. It is contemplated that the applicator cap may be manufactured from a substantially transparent material so as to delineate between the exit surface of the X-ray applicator and a lesion to be treated.

Another embodiment of the present disclosure is directed to a mobile medical care unit. By way of example, the mobile medical care unit may be a bed, a chair, a trolley, a cart, a galley, or a treatment unit. The mobile medical unit may include at least three wheels interconnected by a flexible frame. The flexible frame may be configured to allow automatic adjustment of the height of the wheel when contacting a ground surface. For example, the frame may comprise one or more branches which may be provided with a weak region that may deform under application of the weight of the mobile medical care unit as the mobile medical care unit is moved over the ground. In particular, the frame may include flexible regions, adapted to be resilient and/or bendable under application of the weight of the medical care unit. In one embodiment, the flexible frame includes one or more branches having one or more segments coupled by a spring. Thus, the flexible frame may have an advantage when the mobile medical care unit is transported over an uneven floor, or a floor having irregularities, such as bumps. It will be appreciated that for many applications, it may be desirable that the mobile medical care unit does not change its spatial orientation even when it is transported over an irregular surface. For example, it may be desirable to keep laboratory trays, beds, neonatal beds, and food supply trays, in a substantially constant orientation when transported.

In some embodiments, the mobile X-ray unit according to the foregoing may have an advantage when the base is provided with wheels which are supported by a flexible frame. For example, the mobile X-ray unit may be provided within a vehicle and transported to different treatment locations (i.e., provided as a mobile clinic). In certain circumstances, the treatment may be carried out in inferior conditions. Even treatment in open air is possible. By providing the mobile X-ray unit with a possibility of self-adaptation to the surface irregularities, the adjustment of the X-ray applicator may be carried out in substantially the same way as if the treatment is carried out in a doctor's office. In addition, by ensuring that the X-ray applicator is located in substantially in the same orientation when stored, the doctor would need to go through substantially the same positioning routine when locating the X-ray applicator for treatment. Accordingly, human errors due to a complex three-dimensional handling of the X-ray applicator may be avoided.

These and other aspects of the disclosure will be discussed with reference to drawings wherein like reference numerals or signs relate to like elements. It will be appreciated that the drawings are presented for illustration purposes only and may not be used for limiting the scope of the appended claims.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate embodiments of the invention and together with the description, serve to explain the principles of the invention.

BRIEF DESCRIPTION OF THE DRAWINGS

FIG. 1c presents a perspective view of the mobile X-ray unit shown in FIGS. 1a and 1b, illustrating displacement of a X-ray applicator of the X-ray unit relative to a base of the mobile X-ray unit, according to embodiments of the present disclosure.

FIG. 7, E-E presents a cross-section along line VII-E of the X-ray tube of FIG. 7, according to embodiments of the present disclosure.

FIG. 7, F-F presents a cross-section along line VII-F of the X-ray tube of FIG. 7, according to embodiments of the present disclosure.

FIG. 8 presents a partial schematic view of a medical care unit, such as a mobile X-ray unit, according to embodiments of the present disclosure.

FIG. 9 presents an enlarged view of a flexible frame, according to embodiments of the present disclosure.

FIG. 10 presents another view of the flexible frame shown in FIG. 9, according to embodiments of the present disclosure.

DESCRIPTION OF THE EMBODIMENTS

Reference will now be made in detail to the present embodiment(s) (exemplary embodiments) of the invention, an example(s) of which is (are) illustrated in the accompanying drawings. Wherever possible, the same reference numbers will be used throughout the drawings to refer to the same or like parts.

Figure 1B:
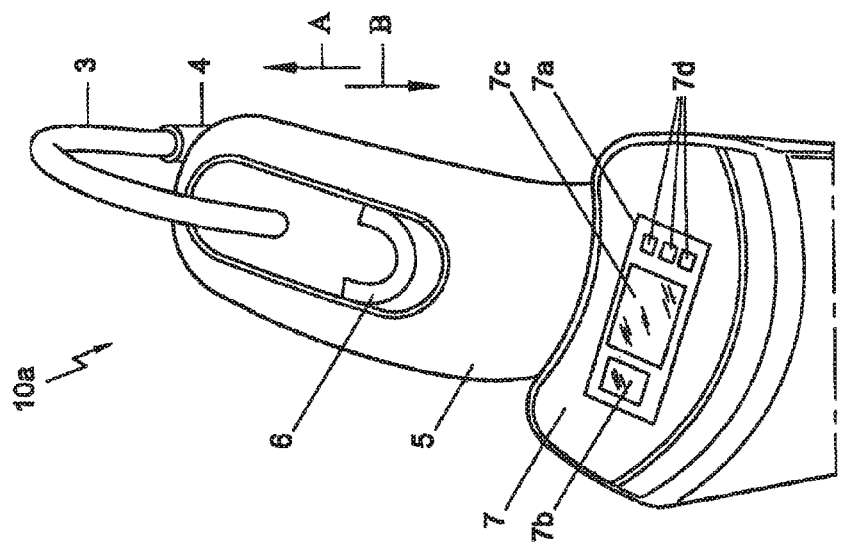
FIG. 1b presents a partial perspective view of a displaceable panel of the mobile X-ray unit illustrated in FIG. 1a, according to embodiments of the present disclosure.
Figure 1A:
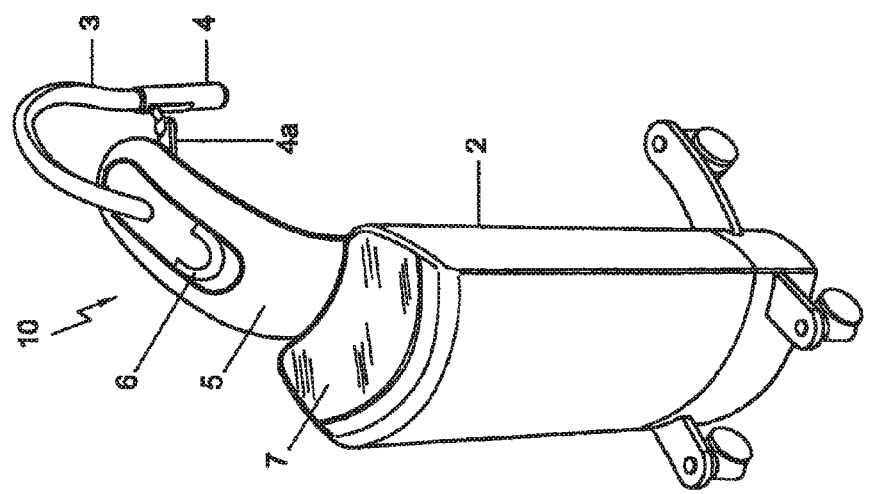
FIG. 1a presents a perspective view of a mobile X-ray unit, according to embodiments of the present disclosure.
Figure 3:
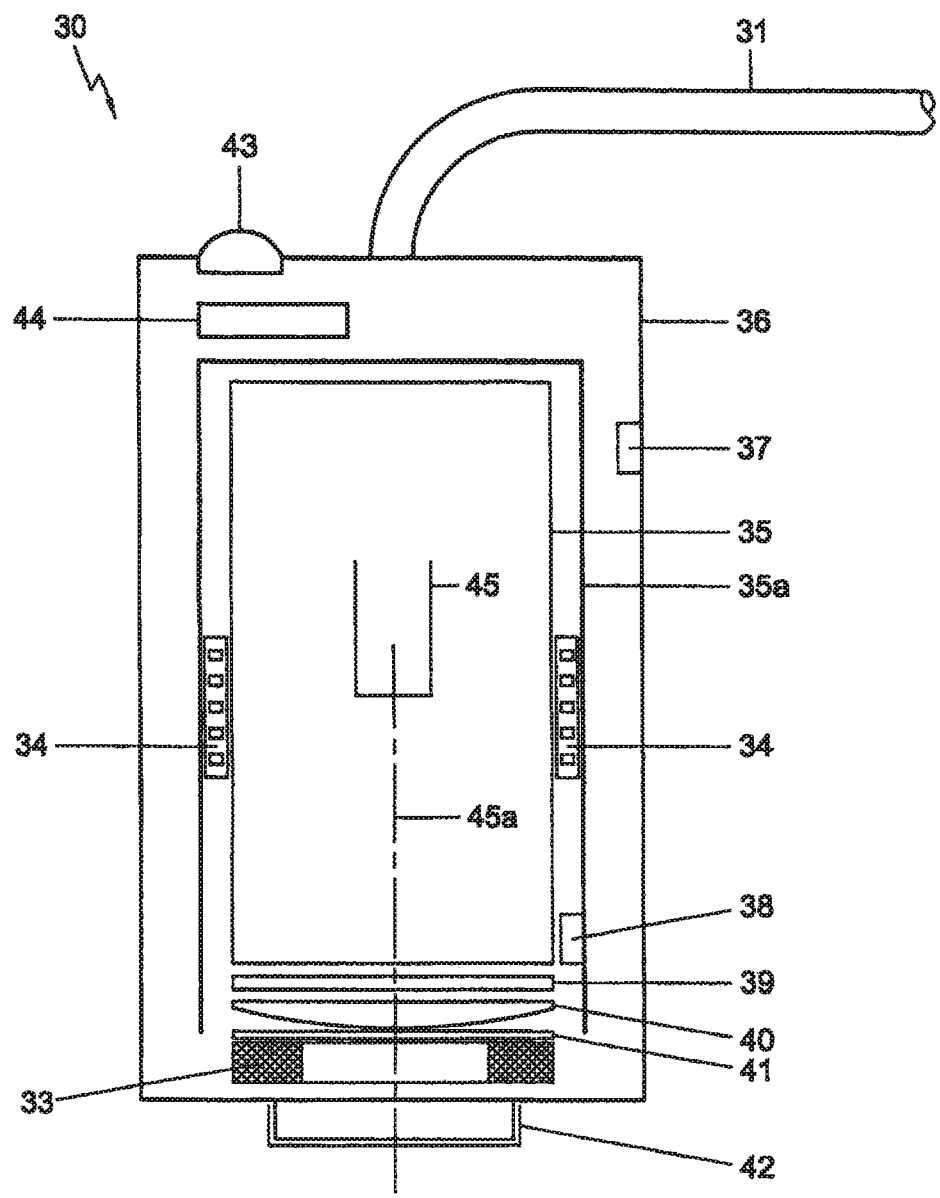
FIG. 3 presents a cross-sectional view of an X-ray applicator of the mobile X-ray unit, according to embodiments of the present disclosure.

FIG. 1a presents a perspective view of a mobile X-ray unit according to an exemplary embodiment of the present disclosure. The mobile X-ray unit 10 may have a base 2 including at least a power supply unit, a cooling system, and a control unit for controlling an operation of an X-ray applicator 4. The X-ray applicator 4 may include an X-ray tube (FIG. 3) disposed in an outer housing (FIG. 3). The X-ray applicator 4 may be connected to the base 2 by flexible cables 3, which may be at least partially received in a displaceable panel 5. The X-ray applicator 4 may be supported by an articulated arm 4a, which may include a pivot for altering the position and/or angle of the X-ray applicator 4 in space. The articulated arm 4a may also be connected to the displaceable panel 5 to vertically displace the X-ray applicator 4. In some embodiments, the displaceable panel 5 is provided with a handle 6 enabling easy manipulation thereof. The displaceable panel 5 may be guided along suitable rails for enabling a substantially smooth and shock-free displacement thereof.

The displaceable panel 5 may be also referred to as a displaceable mast. It may be advantageous to allow the mast to be displaceable along a substantially upright axis with respect to the base 2. It will be appreciated that the substantially upright axis extends in a substantially vertical direction, which is generally upright. However, it will be further appreciated that the terms 'generally upright' or 'substantially vertical' may relate to a direction substantially perpendicular (+−20 degrees) to a plane of the surface on which the mobile X-ray unit is sitting.

The base 2 preferably further comprises a display 7, which may function as a suitable user interface 7a. For example, the patient data, such as a photo of the patient and/or a photo of a lesion may be provided in window 7b, whereby relevant patient information, such as the date of birth, gender, dose prescription and dose delivery protocol and other patient information may be displayed in window 7c. Buttons 7d may be provided as touch functionality for enabling entering data. Alternatively or additionally, suitable hardware switches or buttons may be provided as well.

FIG. 1b presents a partial perspective view of a displaceable panel 5 of the mobile X-ray unit 10, in accordance with an embodiment of the present disclosure. In this enlarged view 10a, specific elements of the displaceable panel 5 are depicted. Accordingly, a handle 6 may be implemented as a mechanical item for pulling or pushing the panel 5. Alternatively, the handle 6 may be arranged as an electrical actuator for triggering motors (not shown) for displacing the displaceable panel 5. For example, when the handle 6 is pulled the motors may be activated for causing the displaceable panel 5 to displace in a direction A. Pushing of the handle 6 may cause lowering of the displaceable panel 5 in a direction B opposite direction A. In some embodiments, the mobile X-ray unit 10 may include stops, limits, or other known structures for limiting the movement of the displaceable panel 5. This may ensure mechanical stability of the system on one hand (limitation of the upper level) and, on the other hand, may be beneficial for preventing cable damage (limitation of the lower level). It is contemplated that the displaceable panel 5 may be movable using built-in rails whose length may be chosen for limiting the displacement range of the panel 5 in a desirable way.

FIG. 1c illustrates the displacement of the X-ray applicator 4 of the X-ray unit 10. In accordance with an aspect of the present disclosure, mobile X-ray unit 10 may be configured so as to support a broad range of translational and rotational movements of the X-ray applicator 4.

In view 11, the X-ray applicator 4 is in a retracted position. It will be appreciated that cabling is not depicted for clarity reasons. The retracted position may be suitable for transport of the mobile X-ray unit 10 towards a booth and/or for maneuvering the X-ray unit 10 around the patient. In order to retract the X-ray applicator 4 as close as possible to the base 2, the articulated arm 4a may be positioned under the outer portion 5a of the displaceable panel 5. For ensuring stability of the mobile X-ray unit 10 during maneuvering thereof, a load block 2a may be provided for lowering the point of gravity of the X-ray unit 10.

In view 12, the X-ray applicator 4 may be in an extended position (i.e., a working position) having an X-ray exit surface 8 oriented towards a patient P. In order to suitably position the X-ray applicator 4 with respect to the patient P, the displaceable panel 5 may be moved to an intermediate position located between the lowest stand position and the highest stand position of the displaceable panel 5. The articulated arm 4a may be used for suitably rotating the X-ray applicator 4 about a rotation axis. in some embodiments, the rotation axis may coincide with a direction in which the X-ray beam is emitted from the exit surface 8 for a vertically oriented X-ray applicator 4.

In view 13, the X-ray applicator 4 may be in a lowered position. For this purpose the displaceable panel 5 may be in its lowest stand position and the arm 4a may be used for orienting the X-ray applicator 4 in a desirable way.

As will be described in more detail in FIGS. 8-10, the base of the mobile X-ray unit may include a set of wheels supported by a frame. The wheels may be interconnected by a deformable frame which ensures that all wheels make contact with an underlying surface, such as a floor or ground, even if such surface is not completely flat. For example, the frame may include one or more branches working together or individually for supporting the wheels of the base. When the weight of the mobile X-ray unit is applied to the frame, the branch may deform to allow the full contact of all of the wheels with the ground. In one embodiment, the frame may include flexible regions, adapted to be resilient and/or bendable under application of the weight of the mobile X-ray unit.

Figure 2:
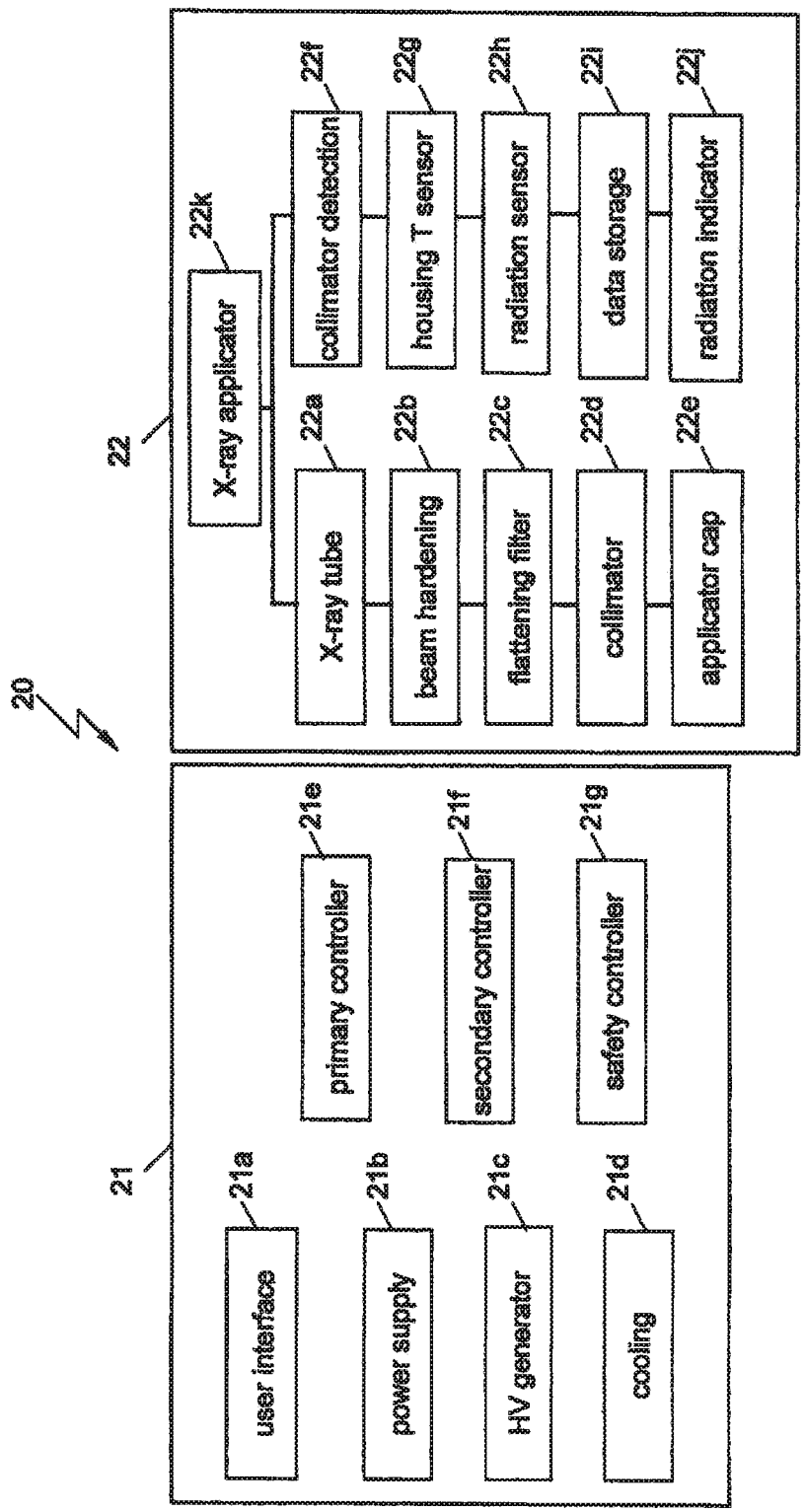
FIG. 2 presents a diagrammatic representation of the mobile X-ray unit, according to embodiments of the present disclosure.

FIG. 2 is a diagrammatic representation of the mobile X-ray unit 10 according to the disclosure. The mobile X-ray unit 10 according to the disclosure includes a high voltage supply, preferably adapted to generate 50-75 kV X-rays in a suitable X-ray tube 22a, a cooling system 21d for cooling the X-ray tube 22a during use, and a control system 21 for controlling electronic and electric parameters of sub-units of the X-ray unit during use. View 20 diagrammatically depicts main units of the control system 21 and of the X-ray applicator 22.

The control system 21 includes a hard wired user interface 21a for enabling switching on and switching off of the high voltage supply 21b. In some embodiments, the high voltage supply 21b comprises a high voltage generator 21c with improved ramp-up and ramp-down characteristics. The high voltage supply is preferably operable for delivering power of about 200 W in use. In some embodiments, the ramp-up time may be of the order of 100 ms. The hard wired interface 21a, may also be arranged to automatically switch on the cooling system 21d when the high voltage generator is switched on. In addition, the control system 21 may include a primary controller 21e arranged for controlling the dose delivery from the X-ray applicator 22 in use. The primary controller 21e may be provided with a primary counter adapted to register time lapsed after the X-ray radiation is initiated. The primary counter may then automatically switch off the high voltage supply 21b to the X-ray tube 22a in the event a pre-determined dose is reached. It will be appreciated that the pre-determined dose is at least dependent on the energy of the X-rays and the dose rate, which may be calibrated in advance. Where calibrated data is made available to the primary controller 21e, adequate primary dose delivery control may be achieved. In some embodiments, a secondary controller 21f may be provided for enabling an independent loop of dose delivery control. The secondary controller 21f may be connected to a dose meter accommodated inside the X-ray applicator 22 in the X-ray field before the collimator 22d. Accordingly, the dose meter may provide real-time data on actual dose delivery taking into account dose variation during ramp up and ramp down of the high voltage source. Still preferably, the control system 21 may include a safety controller 21g adapted to compare readings from the primary controller 21e and the secondary controller 21g for switching off the high voltage generator 21c after a desired dose is delivered. Additionally and/or alternatively, the safety controller 21g may be wired to guard emergency stop, door interlock, and a generator interlock.

In an exemplary embodiment, the X-ray applicator 22 may include X-ray tube 22a housed in an outer housing (shielding) 22k. The X-ray tube 22a may have a target-collimator distance of between 4 and 10 cm, and preferably 5 and 6 cm. The X-ray applicator 22 may further include a beam hardening filter 22b selected to intercept low-energy radiation and a beam flattening filter 22c, designed to intercept portions of X-ray radiation for generating a substantially flat beam profile near the exit surface of the X-ray applicator 22. Further, the X-ray applicator 22 may include one or more collimators 22d arranged to shape the beam. In some embodiments, a set of collimators 22d may be used having, for example, diameters of 1, 1.5, 2, 2.5, 3, 3.5, 4, 4.5, and 5 cm. It will be appreciated that although circular collimators are discussed, collimators of any shape, such as square, elliptic, or custom made collimators are possible. It may be advantageous to have an X-ray applicator 22 with automatic collimator detection device 22f adapted to automatically signal which collimator is being used. In some embodiments, resistive sensing may be used to identify which collimator 22d is being used. In particular, each collimator may be provided with at least a couple of projections for bridging a resistive path provided in a collimator receptacle (FIG. 3). The resulting electrical resistance of the receptacle (FIG. 3) indicates that a collimator is being used.

The X-ray applicator 22 may also include a built-in temperature sensor 22g configured to monitor a temperature of the X-ray tube 22a and/or its shielding 22k. The signal from the temperature sensor 22g may be received by the control system 21 which may carry out the analysis thereof. Should the measured temperature be elevated beyond an allowable level, an alarm signal may be generated. Optionally, a shut-off signal to the high voltage generator may be provided. The X-ray applicator 22 may further include a radiation sensor 22h arranged inside the outer housing 22k for detecting X-ray radiation which may be delivered by the X-ray tube 22a. For safety reasons, the X-ray applicator 22 may include a non-volatile data storage 22i arranged for recording operational parameters at least of the X-ray tube 22a. Further, to enhance radiation safety, the X-ray applicator 22 may be provided with a radiation indicator 22j arranged for providing a visual and/or an audio output to the user and/or the patient regarding ON/OFF condition of the X-ray tube 22a. It will be appreciated that the radiation indicator 22j may include a plurality of signaling devices. In one embodiment, at least one signaling device, for example a light emitting diode (LED), may be associated with the X-ray applicator 22 and provided on the X-ray applicator 22. It is understood, however, that the signaling devices may be positioned at any other location on the mobile X-ray unit.

FIG. 3 presents a cross section of an X-ray applicator of the mobile X-ray unit. The X-ray applicator 30 includes an outer housing 36 and a X-ray tube assembly 35 disposed in the outer housing 36. The X-ray tube 35 may include an external shielding 35a. In use, the X-ray applicator 30 may be maneuvered by the user by holding the housing 32. The X-ray applicator 30 includes an anode 45 configured to emit a beam of X-rays. The anode may have a longitudinal propagation axis 45a. In accordance with one aspect of the present disclosure, the distance between the target (e.g., a perpendicular plate of the anode) and the collimator 33 is in the range between 4 and 10 cm, and preferably 5 and 6 cm. Such a relatively short target-collimator distance may generate an X-ray beam having a substantially narrow penumbra (1.5-1.8 mm for 20/80% lines) and good beam flatness. The X-ray applicator 30 may further include a filter 39 for hardening the X-ray beam emitted from the target 45, a beam flattening filter 40 for flattening out a beam profile, and collimator 33 insertable into a collimator receptacle 41.

A cooling system 34 may be provided so as to prevent overheating of the X-ray tube 35. In one embodiment, the cooling system 34 may be arranged in the space between the X-ray tube 35 and the shielding 35a in contact with the surface of the X-ray tube 35. A suitable coolant may be provided using a pipe 31. It is contemplated that the coolant may be water, a pressurized gas, or even a special oil. The X-ray applicator 30 may further comprise a temperature sensor 37.

The X-ray assembly 30 may further include a suitable radiation detector 38, connected to a radiation indicator 43. Data collected by the radiation detector 38 may be stored in a data storage unit 44.

In order to protect an X-ray exit surface of the X-ray applicator 30 from intra-patient contamination, an applicator cap 42 may be provided to cover at least the exit surface of the X-ray applicator 30. In some embodiments, the applicator cap 42 may be thick enough to fully intercept secondary electrons emanating from the X-ray applicator. The applicator cap 32 may be manufactured from PVDF (polyvinylidene fluoride) and may have a thickness of about 0.4-0.7 mm, and preferably 0.6 mm, across the window portion. The applicator cap may have a density of about 1.75-1.8, and preferably 1.78. Alternatively, the applicator cap 42 may have a thickness of 0.3-0.6 mm, and preferably 0.5 mm, across the window portion. In those embodiments, the applicator cap 32 may have a density of 1.30-1.45, and preferably 1.39. Further, the applicator cap 42 may be manufactured from PPSU (polyphenylsulfone). These materials may be particularly suitable as they as stable under influence of the X-rays and are suitable for different types of sterilization procedures, such as chemical sterilization, or sterilization under elevated temperatures.

Figure 4:
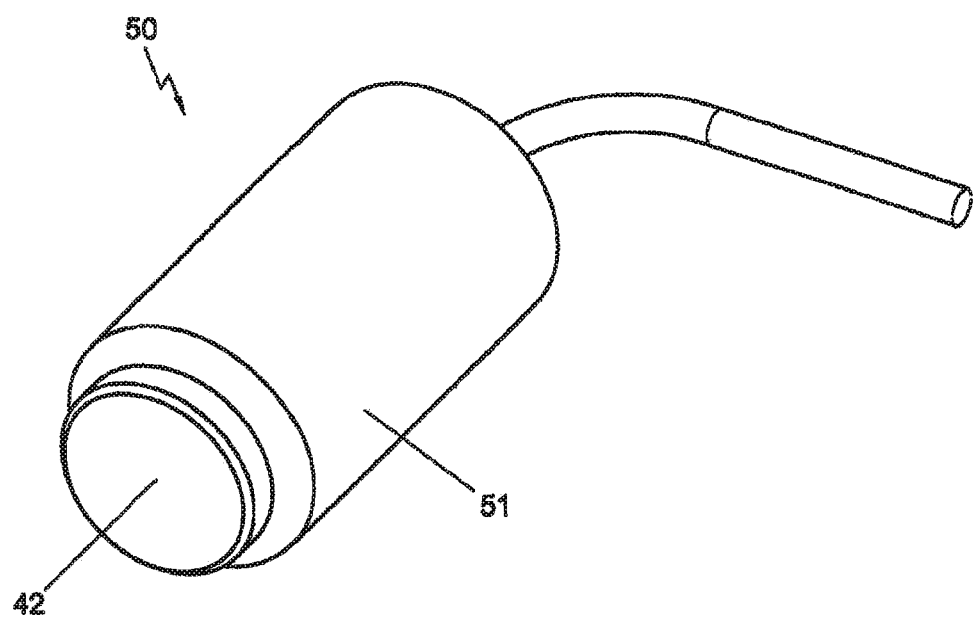
FIG. 4 presents a partial perspective view of the X-ray applicator of FIG. 3 provided with an applicator cap, according to embodiments of the present disclosure.

FIG. 4 presents a partial perspective view of X-ray applicator 4 of FIG. 3 provided with an applicator cap 30. The applicator cap 42 may be manufactured from transparent glass, transparent plastic, or from ceramics as well as from PVDF and PPSU as is set forth above. Applicator cap 42 may also be manufactured from a metal. In the latter case, the applicator cap may be sterilized, otherwise, the applicator cap 42 may be a disposable applicator cap. In view 50 of FIG. 4, it is seen that the outer dimension of the X-ray applicator 51 may be larger that the outer dimension of the exit portion covered by the applicator cap 42 so as to minimize the total weight of the X-ray applicator 51, it is possible that the exit portion has the same dimension as the body of the X-ray applicator 51.

Figure 5:
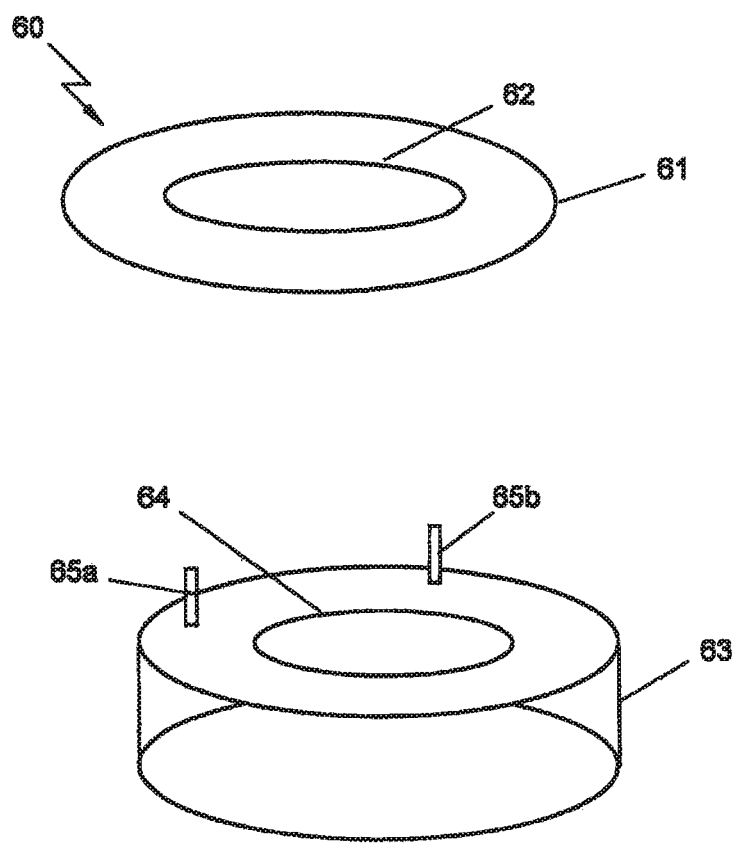
FIG. 5 presents a schematic view of a collimator provided with identification devices, according to embodiments of the present disclosure.

FIG. 5 presents a schematic view of a collimator with identification devices. The collimator 63 may be provided with a central opening 64 for defining a shape and dimension of the resulting X-ray beam emitted from the X-ray applicator 30 as discussed with reference to FIG. 3. The collimator 63 may be adapted to be received in a collimator receptacle 61, which may be shaped as a suitable chamber where the collimator 63 may be firmly fitted. In order to enable automatic collimator identification, the collimator may be provided with two projections 65a, 65b, adapted to interact with a resistive path 62 in the collimator receptacle 61. When the projections 65a, 65b come into contact with the path 62 a net resistance of the collimator receptacle may be changed. The change in the resistance of the collimator receptacle 61 may be used to indicate when the collimator has been inserted in the collimator receptacle 61. It will be appreciated that for a set of collimators, each collimator may be provided with a unique pair of projections leading to a distinguishable change in the net resistivity of the collimator receptacle 61. Those skilled in the art will readily appreciate that a plurality of pairs 65a, 65b may be positioned at different locations on a surface of the collimator 63. Alternatively, it is possible to provide each collimator 63 with an electronic identification device such as, for example, a chip cooperating with a plug. When the plug is plugged-in the collimator receptacle 61 (provided with a cooperating socket), a signal may be transferred to the control unit of the mobile X-ray unit 10.

Figure 6:
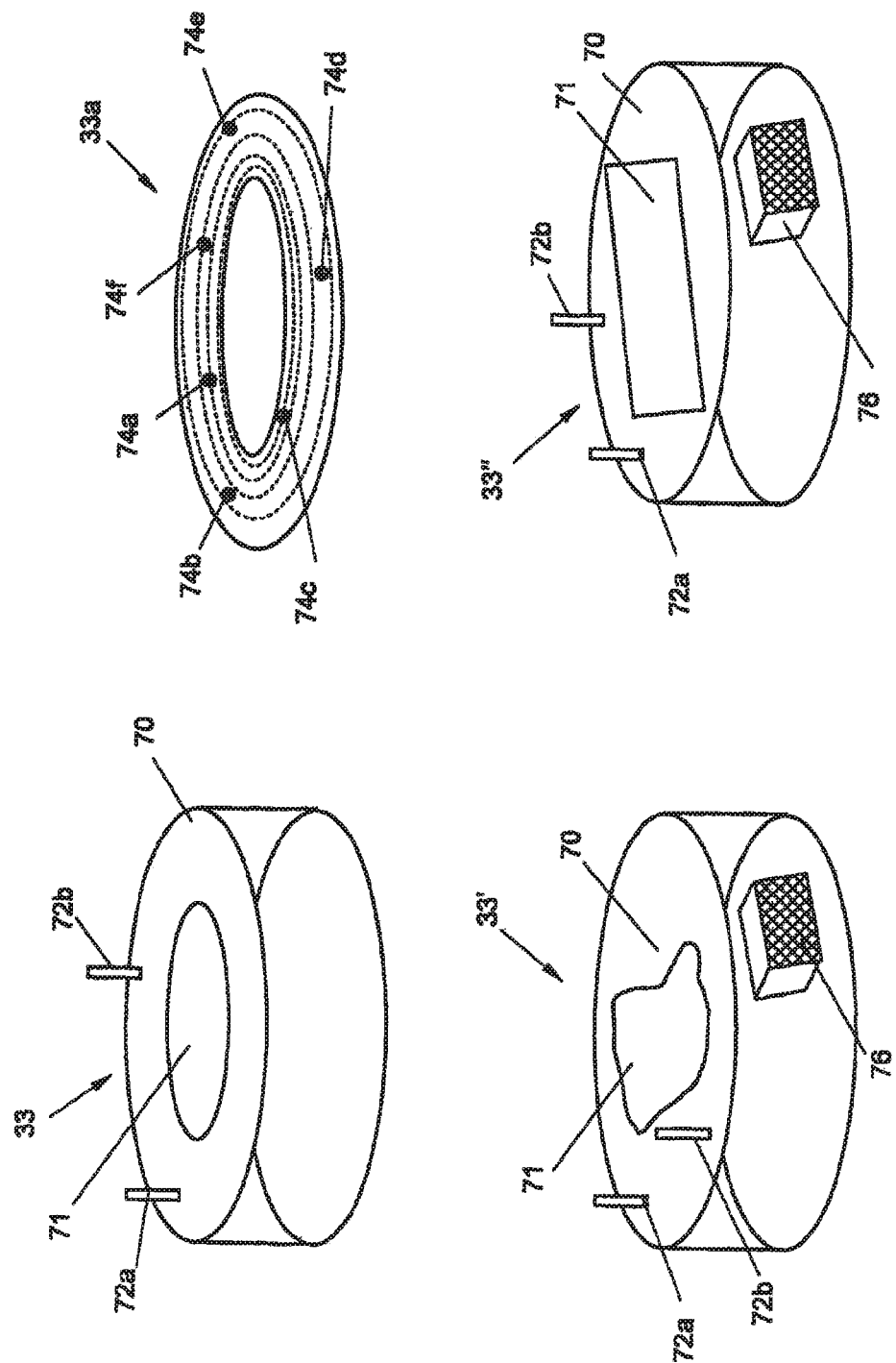
FIG. 6 presents a schematic view of an alternative embodiment of a collimator provided with identification devices, according to embodiments of the present disclosure.

FIG. 6 presents an alternative embodiment of a collimator 33 having identification devices. Different embodiments of a collimator 33, shown in FIG. 3, will be discussed here in more detail. The collimator 33 may be provided with an aperture 71, which may have any shape. The identification device 72a, 72b, may be used for automatically detecting whether a correct (i.e. intended) collimator is being inserted in the X-ray applicator 30. For example, the identification devices 72a, 72b may be spring loaded pins arranged for interacting with a resistive body (shown in the view 33a) for causing a change in a net resistance of the resistive body. By detecting a signal representative of the absolute or relative resistance of the resistive body, a control unit may identify when a collimator is within a collimator receptacle.

In view 33a, a schematic embodiment of the resistive body is depicted, wherein each dot of the series 74a, 74b, 74c, 74d, 74e, 74f is attributed to a separate resistive contact circle (only few are shown for clarity). The net resistive change of the resistive path 33a depends upon where the pin 72a or 72b contacts a resistive circle of the resistive circuit 33a and will change according to the contact positions. The individual collimators of the type 33, may be coded by positioning the contact pins 72a, 72b at different locations on the outer surface 70.

In alternative embodiments, the contact pins 72a, 72b may be supplemented by a contact bar 76, used for locking and/or enabling an appropriate insertion of the collimator 33" into a collimator receptacle. This feature is particularly advantageous for collimators 33" not having rotational symmetry. In a still further embodiment, the collimators and/or the pins may be color coded.

Figure 7:
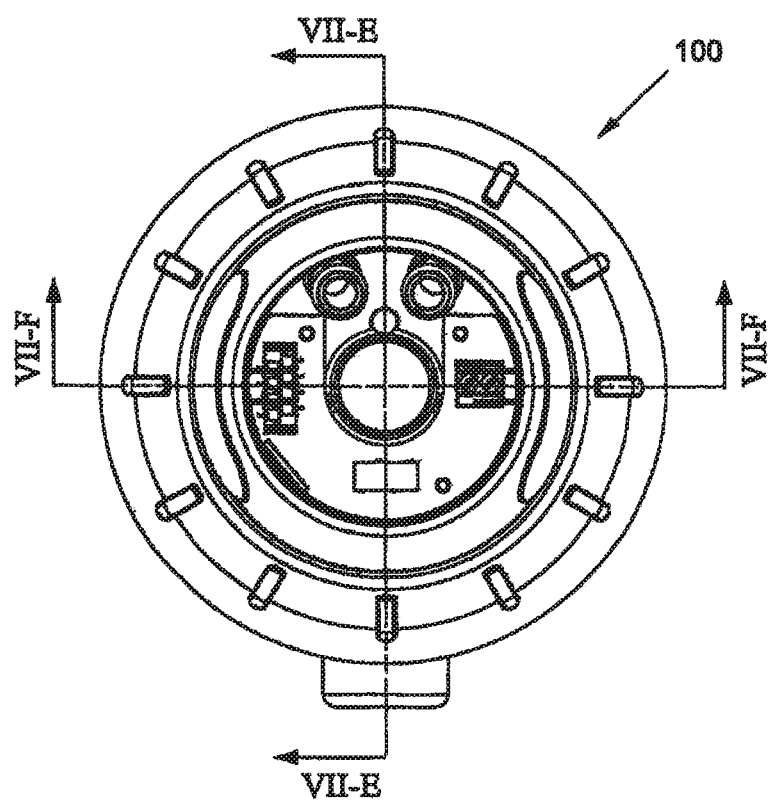
FIG. 7 presents an end view of the X-ray tube, according to embodiments of the present disclosure.

FIGS. 7; 7,E-E; and 7,F-F, illustrate various views of the X-ray tube. The X-ray tube 100 has a body 102 enclosing at one end a window 104 through which the X-rays pass. See FIG. 7 cross-section E-E. The end window 104 may be made from a thin sheet of Beryllium metal. An applicator cap 106 may be positioned over the end window 104 so as to covering the end window 104 and protect end window 104. Applicator cap 106 may be made from a plastic material. The applicator cap may be manufactured from PVDF (polyvinylidene fluoride) and has a thickness of about 0.4-0.7 mm, and preferably 0.6 mm, across the window portion, as described in more detail above. Alternatively, the applicator cap 106 may be manufactured from PPSU (polyphenylsulfone) and have a thickness of about 0.3-0.6 mm, and preferably 0.5 mm, across the window portion, also as described above in more detail.

In the tube body 102 a target 108 is located at a range between 4 and 10 cm from the collimator 130, and preferably between 4 and 5 cm from the collimator 130 (see FIG. 7, cross-section F-F). It will be appreciated that this distance is measured between the outer surface of the target 108 and a midplane of the collimator 130. The target 108 may be made from Tungsten metal to provide the desired X-ray spectrum. The tungsten tip of the target 108 may be mounted on a large anode assembly 110 which also serves to conduct away the heat created from the generation of the X-rays in the target 108. Most of the anode assembly 110 is made from copper. The cathode 112 (see FIG. 7, cross-section F-F) may be located slightly off-axis near the end window 104. Electrons emitted from the cathode are accelerated across the gap by the potential difference between the cathode and anode, in this case set at about 70 kV, to the target 108 where the impact causes the generation of X-rays in a known manner. X-rays emitted from the target 108 pass through a beam hardening filter 122 before passing through a collimator 130 and an exit surface 124 on an applicator cap 106. The collimator 130 may be housed in a suitable collimator receptacle 128.

The anode assembly 110 may be mounted in the body 102 and electrically insulated. One of a number of known techniques and materials can be used to provide the desired level of insulation between the anode assembly 110 and the body 102.

As is well known in the art, the production of X-rays generates large amounts of waste heat. Accordingly, it may be necessary to cool the tube in order to maintain it at a safe temperature. Various cooling mechanisms are known and used in the art. In one embodiment, the X-ray tube 100 is cooled by cooled water forced around the anode region. Cooled water enters the back of the tube by a first conduit 116 and leaves by a second conduit 118 (see FIG. 7, cross-section F-F). The water cooling circuit is a closed loop circuit, with the water leaving the tube assembly 105 to be cooled by a remote cooler (not shown) before returning to the X-ray tube 100. It is contemplated that oil or another liquid may be used as the cooling medium. It is also known that a pressurized gas may be used as an effective coolant in some applications.

As is known in the art, X-rays are generated and emitted in all directions, however the body 102 of the X-ray tube 100 and other internal components will tend to reduce the amount of radiation emitted from the body 102 of the X-ray tube 100 to a minimum, with most of the radiation emitted from the end window 104. The thickness of the shielding provided by the body 102 may be designed so that it provides at least the minimum level of shielding required for safe use by the operator.

A high voltage cable assembly 120 may be connected to the anode assembly 110. The high voltage cable assembly 120 may be connected to a flexible cable (not shown) which in turn may be connected to a high voltage power supply.

A radiation detector 114 may be placed outside the path of the X-ray beam emitted from the target 108 and passing through the end window 104. This detector can be any known radiation detector. In one embodiment, the radiation detector may be a hardened semi-conductor connected to an amplifier. The radiation detector 114 may detect when the tube 102 is working and emitting X-ray energy. Output from the detector 114 may connected to a control unit, and the output signals from the detector 114 may be used to provide an optical indication to a user of whether the tube is operating or not. In this manner, an X-ray detector 114 may be provided which may be used to detect if the X-ray tube is on or off.

With further calibration of the radiation detector 114, it may be possible to determine and calculate the X-ray dose administered to the patient during the treatment. By this means it may be possible to have a real time dosimetry measurement system, in which the precise amount of radiation dose administered can be determined. Once the dose rate is known, a treatment plan can be modified during treatment. This may be advantageous because it may enable a very accurate and carefully controlled dose of X-rays to be administered.

In order to enable the X-ray tube 100 to be placed accurately over a tumour, a tumour illumination device may be is used. The tumour illumination device may include a plurality of lights 126 placed around the circumference of the X-ray tube 100 near the end window 104. When in use, the lights shine onto the skin of the patient. Since the lights 126 are positioned around the circumference of the tube body 102, at a short distance from the end of the X-ray tube 100 they create a circle of light with a sharp cut off of the inner part of the circle. In this way, the position of the lights on the tube body 102 may create a shadow. This shadow circle may be used to indicate the region which will be subject to irradiation when the X-ray tube 100 is turned on. It should be appreciated the area within the circle may not be completely dark; the ambient light may be able to enter the shadow region.

In some embodiments, the lights 126 are white LEDs which can be bright enough to clearly illuminate the target region but do not generate amounts of heat and have very long lives. The lack of heat generation is important because the lights will be in close proximity to the skin of the patient, and so it is important to minimise the risk of burning or other damage to the skin. Other colours of LEDs may be used. Alternatively, other light sources could be used, such as known filament lamps or even a remote light source connected to the ring by fibre optic cables.

FIG. 8 presents a partial schematic view of an embodiment of a medical care unit. In particular, FIG. 8 presents a partial schematic view of a mobile X-ray unit. The mobile X-ray unit may be constructed on a rolling chassis 200. The chassis 200 may be in the shape of an H section. In some embodiments, the legs of the H section are splayed and extend slightly outwards to provide increased stability. The chassis 200 may have four wheels 204 which may be independently rotatable, and may be used to manoeuvre the mobile X-ray unit into a desired position.

The chassis 200 may also be provided with a braking mechanism, which may be operated by a pedal. Twin pedals 220 may be provided, one on each side of the chassis 200. The pedals 220 may be connected by a shaft, thereby ensuring that only one pedal 220 needs to be operated to brake the chassis 200 against movement. The braking mechanism may be arranged to brake diametrically opposed wheels. Other braking mechanisms may be contemplated.

In one embodiment, the chassis legs 201, 202 may be metal channels or beams. The two legs 201 and 202, may be joined by a cross-member 210. The cross-member 210 may be of the C shaped cross-section, and may be secured at or near its ends to the legs 201 and 202 by bolts, welding, or any other method known in the art. It is contemplated that legs 201, 202, and cross-member 210 may have any other shape, size, and/or configuration.

In one embodiment, the legs 201, 202 and cross-member 210 are made from pressed metal parts, however, it is contemplated that legs 201, 202 and cross-member 210 may be formed from any other known material. It is contemplated that the rolling part of the chassis 200 may also be formed from a molded plastic material or, in cases requiring higher strength, load carrying characteristics or rigidity, the rolling part of the chassis 200 may be made from cast metal structures.

A first vertical chassis member 206 may be securely attached to a first one of the legs 201 and may extend upwardly there from. Connected to the second one of the leg 202 is a second vertically extending chassis member 208. Vertical chassis members 206 and 208 are securely connected together by any known method. The operational equipment forming the mobile X-ray unit 10 such as, for example, the high voltage power supply, the cooling system for the X-ray tube, and the control system, may be mounted on the vertical chassis members 206, 208. In addition, the articulated arm (not shown) may be mounted on vertical members 206, 208. This embodiment has an advantage that the vertical chassis members do not need to be vertical but can be upwardly extending at any angle that is convenient and appropriate for the mounting of any ancillary fittings or equipment.

The first chassis leg 201 may be firmly connected to the vertical chassis member 206 by bolts, which facilitate assembly of the chassis 200. However, other known mechanism of securely fixing two components together can be used. The second vertical chassis member 208 may be connected to the second leg 202 by a bearing structure. Second vertical chassis member 208 may be firmly secured to a mounting bracket 214 by bolts, welds, or any other known securing structure. The mounting bracket 214 may be provided with a bearing support which co-operates with corresponding bearing structure in the second leg 202. The bearing structure is conveniently in the form of a shaft or pin 212. Shaft 212 extends through the bearing support in the mounting bracket 214 to form a co-operating support structure in the leg 202. The shaft 212 and co-operating bearing structure enable the second vertical member 208 to rotate about an axis defined as extending along a longitudinal axis extending along the length of the shaft 212. The bearing support may be made of any known form of bearing material, such as a relatively soft metal, such as brass, or from a nylon or polyethylene type plastics material.

In operation, the vertical chassis members 206, 208 may be firmly connected together to provide a strong rigid upwardly extending chassis 200 onto which any other components may be mounted, whilst the rolling part of the chassis may be provided with a flexibility to enable it to accommodate rough or uneven surfaces.

FIG. 9 illustrates a connection between the various components of the flexible frame. It will be appreciated that the construction details for the vertical chassis member 206 may be similar. The shaft 212 may include a rotational axis passing through the centre of the shaft 212 about which the leg 202 can rotate, to allow the rolling part of the chassis 200 to deform and adapt to uneven floors or paths whilst maintaining a relatively stiff upwardly extending chassis portion. The shaft 212 may extend through a bearing support in the mounting bracket 214 into a co-operating support structure in the leg 202 (shown in FIG. 8). This construction allows the legs 201, 202 (shown in FIG. 8) to rotate with respect to one another as they move over (or rest on) uneven surfaces, so as increase the stability of the equipment as a whole.

FIG. 10 presents a further schematic view of the flexible frame shown in FIG. 9. The leg 202 may be mechanically linked by bearing structure 212 (i.e., shaft) through the mounting bracket 214 to the chassis member 208. As described above, the cross-member 210 may be attached at or near each of its ends to one of the legs 201, 202. It, in effect, provides the mechanism keep the legs in their chosen relative positions when the unit is stationary. However, the cross-member may be subject to rotational twisting and torque as the chassis 200 moves over uneven ground. The structural strength of the cross-member 210 may generate forces to resist the twist of the legs with respect to one another, and may also provide a damping effect to restrict and cushion the relative movement of the legs. It will be apparent that the rotational stiffness of the cross-member 210 may be chosen to provide the desired damping effect taking into consideration the weight of the mobile X-ray unit and the un-evenness of the ground being traversed.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A mobile X-ray unit, comprising:
   a base;
   an X-ray applicator connected to the base and comprising an X-ray tube;
   a target element disposed in the X-ray tube and configured to generate an X-ray beam;
   a collimator configured to shape the X-ray beam emitted by the target element, and comprising one or more identification devices;
   a collimator receptacle comprising a resistive circuit having one or more resistive contact positions configured to change a resistance of the resistive circuit when the one or more identification devices contact the one or more resistive contact positions; and
   a controller configured to receive a signal representative of a net resistance or a net resistive change of the resistive circuit after the one or more identification devices contacts the one or more resistive contact positions, and to identify which collimator of a set of collimators is in contact with the collimator receptacle based on the signal.

2. The mobile X-ray unit of claim 1, wherein the one or more identification devices comprise one or more projections.

3. The mobile X-ray unit of claim 1, wherein the one or more identification devices comprise one or more spring loaded pins.

4. The mobile X-ray unit of claim 1, wherein the controller is further configured to determine whether the identified collimator in contact with the collimator receptacle is a correct collimator for the X-ray applicator.

5. The mobile X-ray unit of claim 1, wherein the collimator comprises a circular body having a central opening in a shape configured to define a shape and/or dimension of the X-ray beam.

6. The mobile X-ray unit of claim 5, wherein the circular body has an outer surface from which the one or more identification devices extend.

7. The mobile X-ray unit of claim 1, wherein the collimator comprises a contact bar configured to enable insertion of the collimator into the collimator receptacle in a locking orientation.

8. A collimator identification method for a mobile X-ray unit, comprising:
   detecting a signal representative of a net resistance or a net resistive change of a resistive circuit of a collimator receptacle after one or more identification devices of a collimator contact at least a portion of the resistive circuit when the collimator is positioned with respect to an X-ray applicator of the mobile X-ray unit; and
   identifying which collimator of a set of collimators is in contact with the at least a portion of the resistive circuit based on the signal.

9. The collimator identification method of claim 8, wherein the one or more identification devices comprise one or more projections, and the at least a portion of the resistive circuit comprises a resistive path.

10. The collimator identification method of claim 8, comprising receiving a second signal indicating that an electronic identification device associated with the collimator is received in a socket of the collimator receptacle.

11. The collimator identification method of claim 8, wherein the at least a portion of the resistive circuit comprises a plurality of resistive dots.

12. The collimator identification method of claim 8, comprising determining whether the identified collimator in contact with the at least a portion of the resistive circuit is a correct collimator for the X-ray applicator.

13. A mobile X-ray unit, comprising:
   an X-ray applicator comprising an X-ray tube;
   a target element disposed in the X-ray tube and configured to generate an X-ray beam;
   a collimator configured to shape the X-ray beam emitted by the target element, and comprising one or more projections;
   a collimator receptacle comprising a resistive path configured to interact with the one or more projections, wherein a net resistance of the collimator receptacle is configured to change when the one or more identification devices interact with the resistive path; and
   a controller configured to detect a signal representative of a change in the net resistance of the collimator receptacle after the one or more identification devices interacts with the resistive path, and to identify which collimator of a set of collimators interacted with the collimator receptacle based on the signal.

14. The mobile X-ray unit of claim 13, wherein the collimator comprises a circular body, and the one or more projections extend from a surface of the circular body.

15. The mobile X-ray unit of claim 13, wherein the collimator comprises a central opening configured to define a shape and/or dimension of the X-ray beam.

16. The mobile X-ray unit of claim 13, wherein the collimator receptacle comprises a chamber configured to receive the collimator.

17. The mobile X-ray unit of claim 13, wherein each collimator of the set of collimators comprises a unique pair of projections configured to generate a unique net resistance change when the unique pair of projections interacts with the resistive path.

18. The mobile X-ray unit of claim 13, wherein each collimator of the set of collimators comprises an electronic identification device configured to be received in the collimator receptacle.

19. The mobile X-ray unit of claim 13, wherein the controller is further configured to determine whether the identified collimator that interacted with the collimator receptacle is a correct collimator for the X-ray applicator.

20. The mobile X-ray unit of claim 13, wherein the collimator is disposed within the X-ray tube.

\* \* \* \* \*